US00PP29456P2

(12) United States Plant Patent
Hansen

(10) Patent No.: US PP29,456 P2
(45) Date of Patent: Jul. 3, 2018

(54) ***HOSTA* PLANT NAMED 'WRINKLE IN TIME'**

(50) Latin Name: ***Hosta* hybrid (Tratt.)**
Varietal Denomination: Wrinkle in Time

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 15/530,302

(22) Filed: Dec. 20, 2016

(51) Int. Cl.
*A01H 5/12* (2018.01)
*A01H 5/02* (2018.01)

(52) U.S. Cl.
USPC ..... Plt./353
CPC ..... *A01H 5/02* (2013.01); *A01H 5/12* (2013.01)

(58) Field of Classification Search
USPC ..... Plt./353
CPC ..... A01H 5/02; A01H 5/0272; A01H 5/00; A01H 5/12
See application file for complete search history.

(56) References Cited

PUBLICATIONS

Walters Gardens, Inc. Summer 2016-Spring 2017 catalog, retrieved on Jan. 18, 2018, retrieved from the Internet at https://cld.bz/users/user-9rLuGlj/Walters-Gardens-2017-catalog/204, pp. 1, 6-8, 140, 202-203. (Year: 2016).*

* cited by examiner

*Primary Examiner* — June Hwu

(57) ABSTRACT

A new and distinct *Hosta* plant named 'Wrinkle in Time' with compact rounded-mound habit of dense foliage having blades of wide variegated creamy-yellow developing to creaming-white margins, and dark center with minor intermediate feathering colors. The plant in early summer with compact scapes of closely held horizontal lavender flowers. Foliage has a longitudinal pinching or indentation, tortuous especially when young.

1 Drawing Sheet

Latin name and variety denomination of the plant: Botanical classification: *Hosta* hybrid (Tratt.).

Variety denomination: 'Wrinkle in Time'.

FEDERALLY SPONSORED RESEARCH

This invention was developed without any federally sponsored research or development funding.

BACKGROUND AND ORIGIN OF THE PLANT

The present invention relates to a new and distinct *hosta* plant, *Hosta* 'Wrinkle in Time' hereinafter also referred to as the new plant or just the cultivar name, 'Wrinkle in Time'. *Hosta* 'Wrinkle in Time' was discovered by the inventor as a non-induced, naturally-occurring, whole-plant mutation in a batch of field division propagated *Hosta* 'Pilgrim' (not patented) at a wholesale nursery in Zeeland, Mich., USA in the summer of 2010. The new plant has been asexually propagated by division at the same nursery in Zeeland, Mich., USA since 2012 and also by careful plant shoot tip tissue culture with the resultant asexually propagated plants having retained all the same traits as the original plant. *Hosta* 'Wrinkle in Time' is stable and reproduces true to type in successive generations of asexual reproduction.

No plants of *Hosta* 'Wrinkle in Time' have been sold, under this or any other name, in this country or anywhere in the world, prior to the filing of this application, nor has any disclosure of the new plant been made prior to the filing of this application with the exception of that which may have been disclosed within one year of the filing date of this application and was either derived directly or indirectly from the inventor.

BRIEF SUMMARY OF THE PLANT

There are over 5,600 registered *hosta* cultivars with The American *Hosta* Society, which is the International Cultivar Registration Authority for the genus *Hosta* along with a similar number of unregistered cultivars. The nearest comparison variety is *Hosta* 'Pilgrim', and the new plant differs by having more undulating foliage, especially when young.

Other similar *hostas* include: 'Pilgrim's Progress' (not patented), 'Academy Subtle Sally' (not patented), 'Allan P. McConnell' (not patented), 'Angel Feathers' (not patented), and 'Bob Olson' (not patented). 'Pilgrim's Progress' has flatter leaves and slightly lustrous foliage above and below. 'Academy Subtle Sally' has slightly lustrous adaxial foliage and petioles with reddish spotting. 'Allan P. McConnell' has slightly longer and thinner leaves, the leaf center is slightly more bluish-green, and the margin is more white to creamy white. 'Angel Feathers' has a more cordate leaf blade with wider margins, more feathering of the variegation into the leaf center, and the plant habit is larger and more upright. 'Bob Olson' has a less purple-red stippling in the scape, and none of the above have the undulations of the foliage of the new plant.

Other *Hosta* cultivars have variegated foliage, but 'Wrinkle in Time' is distinct from the above mentioned *hostas* and all other cultivars known to the discoverer by the following combined traits:

1. Compact rounded-mound plant habit with dense variegated foliage;
2. Foliage with wide creamy-yellow becoming creamy-white margins, green center and minor intermediate feathered colors between;
3. Lavender flowers on green scapes with purple stippling; and
4. Leaves with a longitudinal pinching or indentation.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, temperature, source and direction may cause the appearance of minor variation in color.

DETAILED BOTANICAL DESCRIPTION

Figure 1:
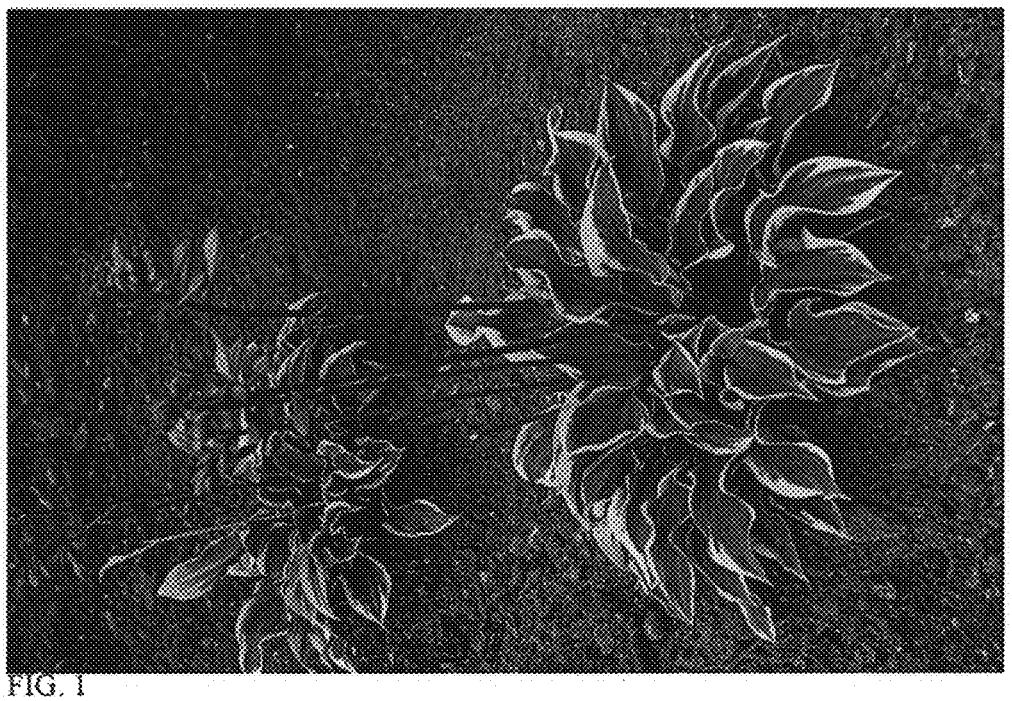
FIG. 1 shows a two-year-old plant grown in a full-sun field with flowers and buds and beginning to develop the creamy-white margins.
Figure 2:
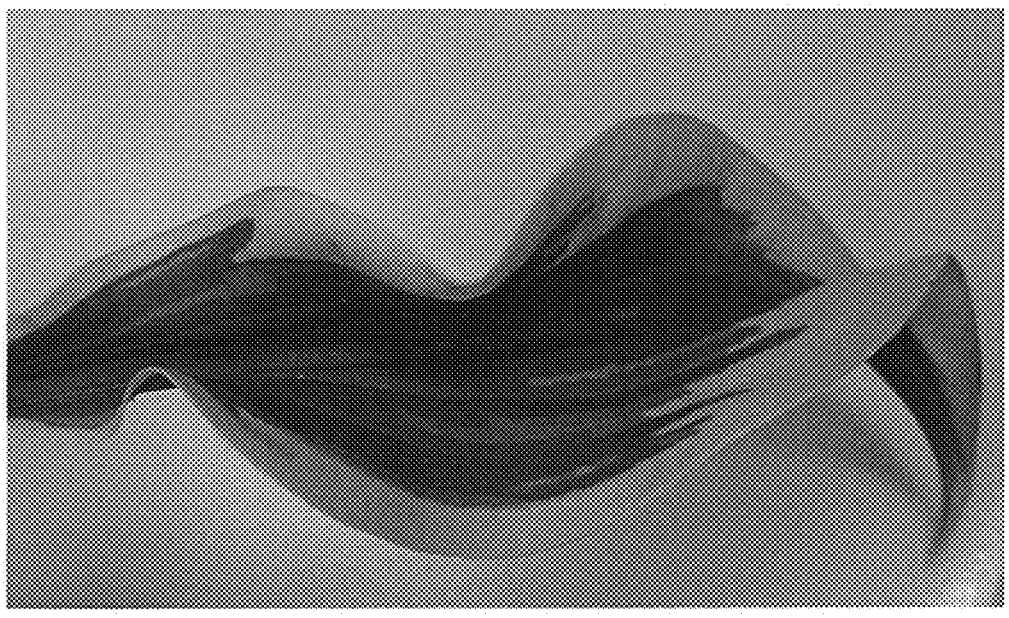
FIG. 2 shows a close-up of a leaf of a two-year-old plant with undulations.

The following descriptions and color references are based on the 2001 edition of The Royal Horticultural Society Colour Chart except where common dictionary terms are used. The new plant, *Hosta* 'Wrinkle in Time', has not been observed under all possible environments. The phenotype may vary slightly with different environmental conditions, such as temperature, light, fertility, moisture and maturity levels, but without any change in the genotype. The following observations and size descriptions are of a potted three-year old plant in a shaded greenhouse in Zeeland, Mich. with supplemental water and fertilizer.

Botanical classification: *Hosta*×hybrid;

Parentage: Whole-plant mutation of *Hosta* 'Pilgrim' (not patented);

Propagation: Garden division and sterile shoot-tip tissue culture;

Time to initiate roots from tissue culture: About two to three weeks;

Growth rate: Rapid;

Crop time: About 10 to 12 weeks to finish during the summer in a one-liter container from rooted tissue culture plantlet;

Rooting habit: Normal, fleshy, lightly branching;

Plant shape and habit: Hardy herbaceous perennial with basal rosette of leaves emerging from rhizomes producing a short symmetrical rounded-mound of leaves;

Plant size: Foliage height about 22.5 cm above soil line to the top of the leaves and about 73.5 cm wide at the widest point slightly above the soil line;

Foliage description: Entire, glabrous, slightly glaucous abaxial and adaxial; lanceolate, single sinuate pinching, slightly tortuous as young plant; acute apex with attenuate base;

Leaf blade size: About 12.7 cm long and 7.6 cm wide; dark green center and creamy-yellow margin developing later in the season to creamy-white that varies in width from 6.0 mm to 14.0 mm wide on leaf blade;

Leaf blade color: Early season shortly and emerging adaxial center color between RHS 137B and RHS 137C; early season adaxial margin nearest RHS 151A; early season abaxial (underside) center nearest RHS 138A; early season abaxial margin nearest RHS 151A; other intermediate colors in irregular patches and stripes between the margin and center portions normally jutting toward the leaf blade center on adaxial comprising irregular streaks and patches nearest RHS 148D and RHS 148C, and abaxial comprising irregular streaks and patches nearest RHS 148C and RHS N144A;

Mid-season and later summer adaxial centers nearest RHS 137A; mid-season and later adaxial margins variably albescent, nearest RHS 11B to nearest RHS 155D; mid-season and later abaxial center nearest RHS 138A; mid-season and later abaxial margins nearest RHS 11C; intermediate colors where adaxial and abaxial leaf blade margins and centers unevenly and irregularly fold over each other comprising irregular streaks and patches of adaxial nearest RHS N138C and RHS 191A, and abaxial irregular streaks and patches nearest RHS 191C and RHS 191B;

Petiole: Entire, glabrous, concavo-convex; mostly straight from base of plant to leaf base with little bending or curving, stiff; average 11.0 cm long and 8.0 mm wide at base;

Petiole color: Adaxial midrib nearest RHS 146A with stripes of between RHS 137A and RHS 137B and margin of about 0.7 mm wide of nearest RHS 160C; abaxial midrib nearest RHS 145D with stripes of between RHS 137A and RHS 137B and margin of about 0.7 mm wide nearest RHS 160C;

Veins: Parallel, costate on abaxial side, normally seven pairs and one main center vein;

Veins color: Adaxial and abaxial veins the same color as the surrounding tissue;

Flower description:

*Buds one day prior to opening*.—Clavate with rounded apex and narrow tubular base; about 1.0 cm diameter toward apex and base narrowing at about mid-length to about 3.0 mm diameter; tube about 1.0 cm long and total bud about 3.0 cm long.

*Bud color*.—Base between RHS N79A and RHS 83B; apical globe between RHS 83B and RHS 83C.

*Inflorescence*.—Average about 42.0 cm tall, flowering in terminal 15.0 cm.

*Flowers*.—Perfect; actinomorphic; funnelform; single; held nearly horizontal with pedicel at about 90° angle to peduncle; about 3.0 cm wide and 4.5 cm long, fused tube portion about 1.2 cm long and 3.5 mm diameter (distal flowers smaller); persists for a normal period, usually one day on plant or as cut flower; scapes remain effective with flowers beginning early summer for about three weeks; about 25 flowers per scape; average spacing between flowers about 0.7 cm.

*Floral bracts*.—Lanceolate, acute apex, truncate partially clasping base; to about 2.8 cm long and 1.0 cm wide; concavo-convex.

*Floral bract color*.—Abaxial nearest RHS 137A with tinting of between RHS 79C and RHS N187A; adaxial nearest RHS 138B with tinting of between RHS 79C and N187B.

*Fragrance*.—None detected.

*Tepal*.—Six; two nearly identical sets of three, glabrous, entire; with acute apex; approximately 4.5 cm long and about 1.0 cm wide.

*Tepal color*.—Coloring of both sets identical; adaxial between RHS N82C and RHS N82D with veins of nearest RHS 79C, base tube portion white, lighter than RHS 155D with veins of nearest RHS 79C; abaxial nearest RHS N82D with veins of nearest RHS 79C; basal tube nearest a blend of RHS 84A and RHS 84B.

*Gynoecium*.—Single; tri-carpelled; Style: single, approximately 4.5 cm long, 0.8 mm diameter, curved upward about 90° in distal 1.5 cm; color lighter than RHS 155D; Stigma: globose, about 1.0 mm in diameter; color nearest RHS 145D; Ovary; oblong, about 5.0 mm long and 2.5 mm diameter at widest; rounded apex and truncate base; color nearest RHS 158B.

It is claimed:

1. A new and distinct ornamental plant cultivar named *Hosta* 'Wrinkle in Time' as herein described and illustrated.

* * * * *